United States Patent [19]

Dulak et al.

[11] Patent Number: 4,888,363

[45] Date of Patent: Dec. 19, 1989

[54] ANHYDROUS COSMETIC PREPARATION

[75] Inventors: Michael P. Dulak, Middletown, N.Y.; Julius R. Zecchino, Kinnelon, N.J.

[73] Assignee: Avon Products, Inc., New York, N.Y.

[21] Appl. No.: 79,060

[22] Filed: Jul. 29, 1987

[30] Foreign Application Priority Data

Jul. 29, 1986 [JP] Japan .................................. 61-178584

[51] Int. Cl.$^4$ ................. C10M 101/00; C10M 113/00
[52] U.S. Cl. ..................................... 514/725; 424/401
[58] Field of Search ....................... 514/458, 179, 725; 424/78, 401

[56]     References Cited
        U.S. PATENT DOCUMENTS 4,457,910  7/1984  Van Cleave ......................... 514/179
4,608,392  8/1986  Jacquet et al. ...................... 514/458
4,751,075  6/1988  Chernowsky et al. ............. 514/458

Primary Examiner—John Kight
Assistant Examiner—Carlos Azpuru
Attorney, Agent, or Firm—S. Michael Bender

[57] ABSTRACT

An anhydrous cosmetic composition is provided comprising an emollient, a thickening agent, a solubilizer, and a working ingredient for enhancing the appearance of or otherwise imparting beneficial effects to the skin. The preferred working ingredient is Vitamin A, or a blend of Vitamin A and derivatives thereof. The composition is exceptionally pleasing and cosmetically appealing when topically applied to the skin's surface, is surprisingly percutaneously absorbent, and maintains the working ingredient stable for extended periods. As a result, lower concentration levels of working ingredients (Vitamin A) are utilized then would otherwise be necessary to achieve improved skin appearance effects, thus avoiding irritation sometimes associated with Vitamin A containing cosmetic preparations.

13 Claims, No Drawings

ANHYDROUS COSMETIC PREPARATION

TECHNICAL FIELD

The present invention relates to cosmetic preparations which may be topically applied to the surface of the skin, and more particularly, to a novel anhydrous cosmetic composition containing at least one ingredient having a beneficial effect with regard to improving the appearance of the skin, and which is exceptionally pleasing and cosmetically appealing when applied to the surface of skin.

BACKGROUND ART

Cosmetic compositions of the oil in water, or water in oil emulsion type are known for delivering beneficial ingredients topically to the skin. Where the beneficial or working ingredient, for example, comprises Vitamin A, or derivatives of Vitamin A, steps must be taken to separate the water phase as long as possible in order to avoid loss of stability and eventual breakdown or inactivity of the working ingredient. One known method of doing this is to package the Vitamin A composition in two separate containers, one housing the aqueous base component and the other housing the Vitamin A ingredient, and then mixing the contents of the two containers together immediately prior to topical application to the skin surface.

Anhydrous cosmetic compositions are also known comprising various admixtures of oily components; however, these generally tend to be greasy, lacking in viscosity, and otherwise less than cosmetically acceptable when topically applied to the surface of the skin.

DISCLOSURE OF THE INVENTION

In accordance with the invention, there is provided a novel anhydrous cosmetic composition comprising an emollient, a thickening agent, a solubilizer, and a working ingredient for enhancing the appearance of or otherwise imparting beneficial effects to the skin. It has been discovered that such composition is exceptionally pleasing and cosmetically appealing when topically applied to the skin's surface, and is surprisingly percutaneously absorbent. As a result, compositions according to the present invention are capable of delivering the working ingredient to the skin's stratum corneum thereby requiring less working ingredient than otherwise would be necessary to achieve beneficial effects. This is extremely significant, when such working ingredient comprises, for example, Vitamin A, or derivatives thereof, because of the latter's tendency to irritate the skin when topically applied in levels or concentrations heretofore believed necessary in order to achieve desired beneficial effects. Thus, the cosmetic compositions contemplated by the present invention may be employed to topically deliver to the skin Vitamin A, or derivatives thereof, in reduced levels sufficient to avoid irritation, yet still achieve the known desired effects of Vitamin A, namely, a reduction in fine lines and wrinkles, a smoothing of the skin's texture, and so on. In addition, since the working ingredient is carried in an anhydrous vehicle or base, its stability and shelf-life are enhanced, and moreover, the entire composition may be packaged in a unitary container.

BEST MODE FOR CARRYING OUT THE INVENTION

To form the novel composition of the present invention, at least one working ingredient capable of imparting beneficial effects to the skin is combined with an anhydrous base or vehicle having cosmetically desirable characteristics.

The anhydrous base is comprised of three major components, namely (i) a liquid emollient, (ii) a thickening agent, and (iii) a solubilizer.

The liquid emollient may consist of any well known type, or mixtures thereof, including ethylhexyl palmitate (EHP) which is mostly preferred; isopropyl myristate (IPM); isopropyl palmitate (IPP); $C_{12-15}$alcohols benzoate; lower molecular weight dimethyl siloxane polymers including hexamethyldisiloxane, polyphenyl methoxysilane, octomethyl cyclotetrasiloxane, or decamethyl cyclopentasiloxane; neopental glycol dicaprate; or ethylene glycol dicaprate; or light mineral oil.

A sufficient quantity of liquid emollient is included in the composition to give it a soothing, supple feel when topically applied to the skin. Generally, up to about 80% by weight of the composition may comprise the liquid emollient, with a range of about 20% by weight to about 45% by weight being particularly preferred.

In accordance with an important feature of the present invention, the thickening agent included in the composition not only imparts consistency but furthermore, gives the resulting formulation an elegant tactile perception. While any thickening agent compatible with the emollient ingredient may be employed to give the desired consistency, such as fumed silica, finely divided silica gel, or stearic acid, for example, it has been discovered that the use of a silicone fluid (polydimethylsiloxane) sold by General Electric Co. under the Trademark "SE-30" surprisingly yields superior tactile properties as well and therefore, is particularly preferred. The aforementioned silicone fluid is a high molecular weight dimethicone material that is gum like in nature having a viscosity in the range of $(0.1-4.0) \times 10^6$ cps. Generally, the amount of thickening agent used in the composition may range from about 0.5 to about 40 percent by weight, with about 10% by weight being mostly preferred.

The solubilizing agent is employed to render the silicone fluid miscible within the emollient and to produce a homogeneous dispersion comprising the working ingredient, the emollient and the thickening agent ingredients. A suitable solubilizing agent compatible with both the emollient and the silicone fluid thickening agent comprises the volatile silicones such as cyclomethicone pentamer and/or cyclomethicone tetramer which are preferably used in the composition alone or in combination, with a 1:1 blend being particularly preferred. Generally, the cyclomethicone solubilizing agent will be present in an amount ranging from about 10% to about 90% by weight with about 60% by weight being mostly preferred. Cyclomethicone has many of the desirable properties of an emollient. Thus, if desired, the emollient phase may be replaced entirely in the preferred composition by cyclomethicone, or more preferably, a blend of cyclomethicone pentamer and tetramer.

It is well known that various working ingredients may be included in cosmetic preparations to impart beneficial effects to the skin. Erlemann[1] and Jarrett et al.[2] describe such beneficial effects resulting from the use of various vitamins as the working ingredient in topically applied cosmetic preparations. In the present invention, Vitamin A (Retinol), and more particularly, a mostly preferred blend of Retinol and other known compounds having Vitamin A activity, is employed as the especially preferred working ingredient. The mostly preferred Vitamin A blend comprises a mixture of Retinol, retinyl acetate, retinyl palmitate, carotene, a surfactant such as polysorbate, and suitable anti-oxidants such as butylated hydroxytoluene (BHT), and butylated hydroxyanisole (BHA), with the active Vitamin A compounds comprising about 50% by weight of the blend.

(1) G. E. Erlemann, Vitamine in der Kosmetik. Seifen-Ole-Fette-Wasche. 110(1984) 181.
(2) A. Jarrett, R. J. Jackson, The effects of Vitamin A on the skin and its role as a cosmetic agent. IFSCC, 11th, Cosmetic Technology and Science. (1980) 141.

In the preferred composition, the Vitamin A blend or working ingredient may comprise from about .002 to about 2% by weight, and most preferably about 0.02% by weight. Ideally, the degree of benefit imparted to the skin will depend upon the concentration level of active Vitamin A compounds. In prior water-based compositions, the Vitamin A compounds are unstable and decompose quickly requiring a (i) relatively high concentration levels which in turn, may lead to skin irritation, or (ii) elaborate measures e.g., separate containers. In the preferred anhydrous composition of the present invention, however, the Vitamin A compounds remain stable over a long period of time. What's more, it has been discovered that the preferred composition is highly percutaneously absorbent and penetrates quickly and easily to the stratum corneum layer beneath the skin surface layer (epidermis). As a result of these advantageous factors, namely, long-term stability and high rate of percutaneous absorption, lower concentration levels of the working ingredient, namely, the active Vitamin A compounds, may be employed in the preferred composition than otherwise would be necessary to achieve perceptible skin appearance improvements such as reduction in fine lines and wrinkles, increased smoothness in texture, increased lustre, and healthier looking tone, all of the while avoiding irritation of the skin sometimes associated with Vitamin A containing cosmetic preparations.

In addition, the anhydrous base or vehicle resulting from the aforementioned combination of emollient, thickening agent, and solubilizing agent is surprisingly smooth, non-greasy, and elegant in terms of its tactile preception, thus yielding an exceptionally pleasing and cosmetically appealing product. Moreover, the composition of the invention exhibits excellent properties as a skin moisturizer.

In making the composition of the invention, the preferred procedure comprises the formation of a first phase by admixing the emollient, working ingredient and solubilizing agent in a suitable blender. A second phase is then formed by blending the solubilizing agent and thickening agent together. Finally, the first and second phases are blended together.

It will be appreciated that during the formation of the first and second phase, the usual additional ingredients normally included in cosmetic preparations such as sun-screens, anti-oxidants, preservatives, fragrances, colorants and the like may be added in suitable quantity to the blend.

The present invention will now be further described with reference to the following illustrative examples which are not to be construed as limiting.

EXAMPLE 1

A preferred anhydrous composition in accordance with the invention was formulated as follows (all quantities are stated as weight percents):

A Vitamin A blend (working ingredient) was formulated containing:

| | |
|---|---|
| 48.01276% | Polysorbate 20 |
| 48.01276% | Retinol |
| 3.00000% | BHT |
| .75000% | BHA |
| .09977% | Retinyl Acetate |
| .09977% | Retinyl Palmitate |
| .02494% | Carotene |
| 100.00000% | |

A first phase was formed by mixing a 1:1 cyclomethicone blend (Tetramer and Pentamer) together with silicone fluid (SE-30) for 1½ to 2 hours at room temperature in a mixing vessel. The above Vitamin A blend, together with an emollient (EHP), can additional quantity of the 1:1 cyclomethicone blend, anti-oxidants and preservative, were separately mixed at room temperature for about 20 minutes in a similar mixing vessel to form a second phase. The second phase was then added to the first phase while mixing continued for a period of 20 minutes at room temperature to form the following composition suitable for application to the skin:

| | |
|---|---|
| 29.00000% | Ethylhexyl Palmitate |
| 29.89500% | Cyclomethicone-Pentamer |
| 29.89500% | Cyclomethicone Tetramer-Pure |
| 10.00000% | Silicone Fluid SE-30 |
| 0.09200% | Butylated Hydroxytoluene |
| 0.09800% | Butylated Hydroxyanisole |
| 0.02000% | Vitamin A Blend (Example 1) |
| 1.00000% | 2-Phenoxy Ethanol |
| 100.00000% | |

The resulting composition comprised a low viscosity (approximately 1000 cps), clear, almost transparent liquid which when topically applied to skin exhibited a silky smooth, non-greasy, dry, soft and elegant tactile sensation. When rubbed into the skin, it appeared to be absorbed immediately.

EXAMPLE 2

The composition prepared in accordance with Example 1 was tested for stability of the working ingredient over a 3 month period by placing 2 oz. samples in glass jars sealed by aluminum foil, and then storing the jars at room temperature and 100° F., respectively. The samples were assayed for Vitamin A activity by measuring the quantity of Vitamin A using standard high pressure liquid chromatography techniques at the commencement of the test and at one-month and three-month intervals, respectively. The amount of Vitamin A by weight percent measured for each sample was as follows:

| | Room Temperature | 100° F. |
|---|---|---|
| Start | 0.0100% | 0.0100% |
| 1 Month | 0.0100% | 0.0085% |
| 3 Months | 0.0080% | 0.0065% |

These results indicate excellent stability of the working ingredient in the anhydrous composition of the present invention.

EXAMPLE 3

Following the procedure of Example 1, a composition was prepared in accordance with the invention having the following formulation:

|  | | |
|---|---|---|
| | 29.00000% | Ethylhexyl Palmitate |
| | 59.75000% | Cyclomethicone Tetramer-Pure |
| | 10.00000% | Silicone Fluid SE-30 |
| | 0.09200% | Butylated Hydroxytoluene |
| | 0.09800% | Butylated Hydroxyanisole |
| | 0.06000% | Vitamin A Blend (Example 1) |
| | 1.00000% | 2-Phenoxy Ethanol |
| Total | 100.00000% | |

A Franz diffusion cell was then used to measure the percutaneous absorption of the composition. Skin from the back of adult female hairless mice was excised and the muscle tissue carefully disected away from the dermal side. The pieces were mounted epidermal side up in the diffusion cell with an area of 0.78 cm$^2$ exposed. Isotonic saline was used in the receptor compartment, which was stirred continuously. A sample of the composition was spiked with a radioisotope of Retinol [11,12 (n) $^3$H]obtained from Amersham Corporation, Arlington Heights, Illinois, sufficient to achieve an activity of 3–4×10$^9$ dpm/ml. A volume of 10 μl of the spiked base was next applied to the mounted skin. Samples of 50 μl were then removed from the receptor compartment over a period of 72 hours and added to 5 ml of Packard Scint A liquid scintillation cocktail. These were left for 24 hours to allow any chemiluminescence to decay. They were then quantitated using a Packard Tri-Carb 4640 liquid scintillation counter. The percentage of the applied dose absorbed after 72 hours was 36.89 ±7.03 (n=6). Similar percutaneous absorption tests conducted on a control composition comprising Retinol in a known silicone emulsion base resulted in the applied dose being absorbed over 72 hours measuring in the range of 6–10. thus indicating that the percutaneous absorption of the present composition is capable of delivering approximately 4 times more working ingredient (Vitamin A) through the epidermal layer than the control.

EXAMPLE 4

The composition of Example 3 was tested over a period of 14 days by a panel of twenty-eight middle-aged female subjects having a moderate amount and depth of lines in the crowsfeet area. Each panelist applied the composition daily to only one side of her face and left the otherside untreated. Trained evaluators, having no knowledge of the treated side, rated each panelist daily on both sides of the face for line frequency and depth. In addition, each panelist was given a questionnaire for self evaluation following the test period. After 11 days, the trained evaluators found a significant reduction of lines in the crowsfeet area on the treated side of the face.

With respect to the panelists' own self-evaluation, the mean scores reflecting the extent of agreement to the following perceived benefits following completion of 14 day test are tabulated as follows:

| | Mean Scores ± S.D. |
|---|---|
| my skin looks younger | 4.3 ± .9 |
| my skin looks more moist | 4.2 ± .7 |
| my skin has fewer lines | 4.3 ± .9 |
| my skin feels smoother | 4.4 ± .7 |
| my skin looks healthier | 4.2 ± .9 |
| my skin has a brighter sheen | 4.1 ± .8 |
| my skin feels softer | 4.4 ± .7 |
| my skin looks firmer | 4.4 ± .7 |
| my skin looks better | 4.5 ± .7 |
| my skin shows fewer signs of aging | 4.4 ± .8 |
| my skin looks smoother | 4.5 ± .6 |
| my skin has visibly improved | 4.5 ± .7 |

The mean scores were calculated using the following scale:
5=Agree Strongly
4=Agree Somewhat
3=Neither Agree nor Disagree
2=Disagree Somewhat
1=Disagree Strongly The above results indicate that the composition of the present invention imparts perceived beneficial effects to the skin with regard to appearance, i.e., lines and wrinkles are reduced, smoothness and sheen improved, and other visable signs of premature aging diminished.

EXAMPLE 5

The rhino mouse (AAI:RH-hr$^{rh}$) is a suitable model for assessing substances that affect epithelial differentiation. The composition of Example 1 in amount of 0.1 ml was applied topically once per day to the dorsal skin surfaces of 4 rhino mice over a six week period. Skin biopsies were then taken at the end of week 3 and of week 6, H&E stained, and assessed histologically (light microscopy) by 2 independent observers for (1) percent elimination of utriculi (pseudocomedones) and (2) increased epidermal thickness. Compared to untreated control animals, both observers recorded a statistically significant increase in both of these parameters for the animals treated with the composition of Example 1. The changes indicate that the composition of the present invention imparts retinoid effects to the skin which result in observable improvements to the structured biomatrix and function thereof.

EXAMPLE 6

The composition of Example 3 was tested for skin moisturizing efficacy by a panel of 12 male and female subjects. Each panelist was instructed to wash his/her hands with plain soap hourly over a 5 hour period. Each panelist was then subjected to a standard stereomicroscopic dryness evaluation by 2 trained evaluators to determine a "starting dryness rating" in accordance with the following scale:

Stereomicroscopic Dryness Rating Scale

1. No observable scale at 30×magnification.
2. Occasional scale, not necessarily uniformly distributed, either on plateau or in sulci. p0 3. Pronounced scaling (visible with the naked eye giving the skin surface a whitish appearance). Hand is rough to the touch.
4. More scale and pronounced separation of scale edges from skin, although they may still be lying flat on the skin surface. Some evidence of cracking in sulci and on plateau.

5. Extensive cracking of skin surface, in some cases scales are very large.
6. Pronounced large and small scaling overall of skin surface, the scales having curls raised outer edges, with extensive cracking in sulci, leaving practically no normal skin visible.
7. Absolutely no normal skin visible. Cracking and dryness covers the entire surface, which is completely white to the naked eye.

A 0.20 cc aliquot of the composition was then applied to the back of one of the hands of each panelist in such manner as to tend to balance the dryness rating between the treated and untreated hands of each subject and to equalize the total starting dryness ratings for both groups of test and control hands. After waiting one hour following application of the composition, the back of each panelist's hands were again subjected to stereomicroscopic evaluation and graded for dryness by the trained evaluators. Analysis of variance of the "dryness rating" scores was conducted by computer and an F ratio of 73.32 was measured thus indicating that the composition is an excellent instantaneous moisturizer ($F \geq 4$ means a confidence level of 95%).

In view of the above, it should be apparent that the anhydrous cosmetic preparation of the present invention has many advantages over prior compositions. Although specific preferred forms of the invention have been disclosed for purposes of illustration, many additional changes and modifications may be made. For example, working ingredients other than Vitamin A, and derivatives thereof, may be employed in the anhydrous vehicle of the present invention to impart cosmetic or pharamacological benefits to the skin. Such other working ingredients contemplated include for example, tanning accelerators, anti-acne preparations, other vitamins, analgesics, and hormones, it being understood that these must be compatible with the remaining ingredients of the disclosed compositions. Accordingly, the present invention should be limited only by the true spirit and scope of the appended claims.

We claim:

1. A cosmetic or therapeutic composition comprising:
   an emollient, said emollient being present in an amount in the range of about 20% to about 45% by weight;
   a thickening agent, said thickening agent being present in an amount in the range of about 0.5% to about 40% by weight;
   a solublizing agent for rendering the thickening agent miscible in said emollient, said solublizing agent being present in an amount in the range of about 10% to about 90%, said solublizing agent, said thickening agent and said emollient forming an anhydrous carrier, and
   a working ingredient dispersed throughout said anhydrous carrier, said working ingredient being present in an amount in the range of about 0.002% to about 2% by weight, said working ingredient comprising Vitamin A or its derivatives, said anhydrous carrier being percutaneously absorbable by human skin and said working ingredient being rendered stable in carrier.

2. The composition of claim 1 wherein said working ingredient comprises Vitamin A.

3. The composition of claim 1 wherein said working ingredient comprises a blend of Vitamin A compounds.

4. The composition of claim 3 wherein said blend of Vitamin A compounds comprises Retinol and one or more of the following ingredients: retinyl acetate, retinyl palmitate and carotene.

5. The composition of claim 1 wherein said thickening agent comprises polydimethylsiloxane.

6. The composition of claim 1 wherein said emollient comprises ethylhexyl palmitate or isopropyl palmitate, or isopropyl myristate, or $C_{12-15}$ alcohols benzoate, or light mineral oil, or mixtures thereof.

7. The composition of claim 1 wherein said solubilizing agent comprises a volatile silicone.

8. The composition of claim 7 wherein said volatile silicone comprises cyclomethicone pentamer or cyclomethicone tetramer.

9. The composition of claim 8 wherein said volatile silicone comprises a 1:1 blend of cyclomethicone pentamer and cyclomethicone tetramer.

10. The composition of claim 1 wherein said working ingredient comprises Vitamin A in an amount ranging between about 0.001% and about 1.00% by weight.

11. The composition of claims 1 whereas the amount of said emollient is about 29% by weight, the amount of said thickening agent is about 10% by weight, and the amount of said solubilizing agent is about 60% by weight.

12. The composition of claim 1 wherein said emollient and said solubilizing agent comprise cyclomethicone.

13. The composition of claim 12 wherein said cyclomethicone comprises cyclomethicone pentamer or cyclomethicone tetramer, or, mixtures thereof.

* * * * *